US006620794B1

(12) United States Patent
O'Lenick, Jr. et al.

(10) Patent No.: US 6,620,794 B1
(45) Date of Patent: Sep. 16, 2003

(54) GUERBET FUNCTIONALIZED PHOSPHOLIPIDS

(75) Inventors: Anthony J. O'Lenick, Jr., Dacula, GA (US); Kevin A. O'Lenick, Dacula, GA (US)

(73) Assignee: Colonial Chemical Inc., South Pittsburg, TN (US)

( * ) Notice: Subject to any disclaimer, the term of this patent is extended or adjusted under 35 U.S.C. 154(b) by 0 days.

(21) Appl. No.: 10/189,747

(22) Filed: Jul. 8, 2002

(51) Int. Cl.[7] .............................. A61K 31/00; C07F 9/05
(52) U.S. Cl. ............................................. 514/41; 514/77
(58) Field of Search ........................ 554/41; 424/70.28; 514/77

(56) References Cited

U.S. PATENT DOCUMENTS

| | | | | |
|---|---|---|---|---|
| 4,209,449 A | * | 6/1980 | Mayhew et al. ............... | 554/41 |
| 4,243,602 A | | 1/1981 | O'Lenick | |
| 4,382,036 A | * | 5/1983 | Lindemann et al. .......... | 554/41 |
| 4,822,529 A | * | 4/1989 | Saiki et al. .................... | 554/41 |
| 5,019,281 A | * | 5/1991 | Singer et al. ................ | 252/8.63 |
| 5,415,855 A | * | 5/1995 | Critchley et al. ............. | 424/61 |
| 6,180,806 B1 | * | 1/2001 | O'Lenick et al. ............. | 554/52 |
| 6,451,775 B1 | * | 9/2002 | Smith et al. .................. | 514/77 |

* cited by examiner

Primary Examiner—Jean F. Vollano

(57) ABSTRACT

The present invention relates to novel compositions and, more particularly, to a class of compounds having specific quaternized amine based upon a guerbet amido amine linked to specific phosphate esters. Guerbet acids are a specific group of branched acids that have no unsaturation present in the group, but nonetheless are liquid, and are outstanding skin care emollients, providing great spreadability on the skin. In addition this material is not toxic to human skin and is well tolerated by human tissue making it suitable for use in the preparation products for personal care applications.

20 Claims, No Drawings

GUERBET FUNCTIONALIZED PHOSPHOLIPIDS

FIELD OF THE INVENTION

The present invention relates to novel compositions and, more particularly, to a class of compounds having specific quatemized amine based upon a guerbet amido amine linked to specific phosphate esters. Guerbet acids are a specific group of branched acids that have no unsaturation present in the group, but nonetheless are liquid, and are outstanding skin care emollients, providing great spreadability on the skin. In addition this material is not toxic to human skin and is well tolerated by human tissue making it suitable for use in the preparation products for personal care applications.

BACKGROUND OF THE INVENTION

Phosphate ester and quaternary amine compounds are well known and have been widely used for many years More recently, various betaine-type derivatives having, in general, quaternized alkyl amine groups and at least one phosphorous-containing anion in the molecule referred to hereinafter as "synthetic phospholipids", have been disclosed The in U.S. Patents are U.S. Pat Nos. 3,856,893 and 3,928,509 to Diery et al. Diery discloses that the phosphonate compounds of his invention are active anti-microbial compounds. Later amido amine and imidazoline derivatives were disclosed for example, in U.S. Pat. Nos. 4,215,064; 4,233,192 and 4,380,637 to Lindemann et al., U.S. Pat. Nos. 4,209,449; 4,336,385 and 4,503,002 to Mayhew et al., and U.S. Pat. Nos. 4,243,602; 4,283,542 and 4,336,386 to O'Lenick et al. These synthetic phospholipids are suggested as exhibiting an outstanding combination of surfactant characteristics as well as being well tolerated by human tissue, i.e., they exhibit exceptionally low ocular irritation and oral toxicity. While these known phospholipids have been found useful as surfactants in a variety of personal care, they have not exhibited an ability to protect the skin from irritation or provide barrier properties to the skin, protecting it from the negative effects of chemicals and environmental effects.

Guerbet alcohols have been known for over 100 years now. Marcel Guerbet pioneered the basic chemistry in the 1890s. It has allowed for the synthesis of a regiospecific beta branched hydrophobe which introduces high purity, branching into the molecule. The ability to capitalize upon this reaction sequence and develop derivatives has resulted in many materials that find use in applications where liquidity and lubrication are important. The various market segments include metal lubrication, plastic mold release, paper processing, synlube, and personal care. The chemistry results in a unique class of materials that remains underutilized to this day.

Guerbet Alcohols, the oldest and best-understood material in the class of compounds, have been known since the 1890's when Marcel Guerbet first synthesized these materials. The reaction sequence, which bears his name, is related to the Aldol Reaction and occurs at high temperatures under catalytic conditions. The overall reaction can be represented by the following equation;

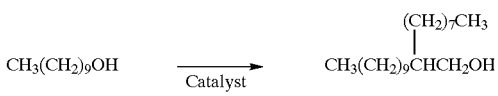

A relatively new Guerbet derivative is the Guerbet acid. They are prepared by the oxidation of Guerbet alcohols to produce primary carboxylic acids. One method by which this can be achieved is the dehydrogenation of the alcohol with alkali metal salts, called oxidative alkali fusion, which gives excellent yields of carboxylic acids.

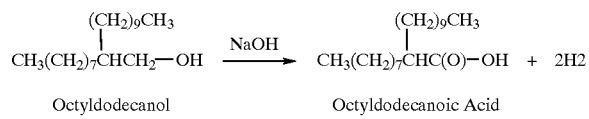

It is very desirable to provide a material from aqueous solution that will protect the skin from environmental irritants such as ozone, and other pollutants. The compounds of the present invention can be formulated into body washes and other skin products and protect the skin from damage. The added properties of not being subjected to rancidity, an oxidative process that affects unsaturated compounds, and having outstanding spreadability on the skin make these compounds unique cosmetic additives.

SUMMARY OF THE INVENTION

Objective of the Invention

It is the objective of the invention to provide a novel guerbet based phospholipid and a process of its use, which comprises using it as an emollient and softener for skin in personal care applications.

Detailed Description of the Invention

In accordance with the present invention we have now been discovered novel phospholipid compound, which conform to the following structure:

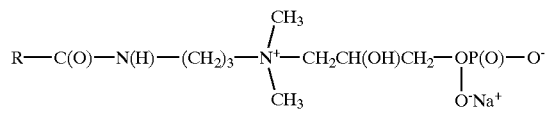

wherein;
R is

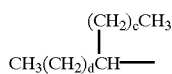

c and d are each integers ranging from 3 to 19 with the proviso that d=c+2.

The present invention is directed toward a process for conditioning skin that comprises contacting the skin with an effective conditioning amount of a phospholipid compound, which conforms to the following structure:

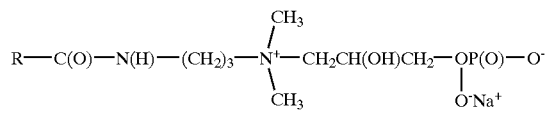

wherein:
R is

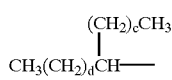

c and d are each integers ranging from 3 to 19 with the proviso that d=c+2.

The effective conditioning concentration ranges from 0.1% to 15%. by weight of the phospholipid. In a preferred embodiment the effective conditioning concentration ranges from 1.0% to 5% by weight of the phospholipid.

Preferred Embodiments

In a preferred embodiment the effective emulsifying concentration ranges from 0.5% to 25% by weight with 3 to 15% being the preferred concentration.

In a preferred embodiment of the novel phospholipid c is 13 and d is 15.

In a preferred embodiment of the novel phospholipid c is 17 and d is 19.

In a preferred embodiment of the novel phospholipid c is 3 and d is 5.

In a preferred embodiment of the novel phospholipid c is 4 and d is 6.

In a preferred embodiment of the novel phospholipid c is 5 and d is 7.

In a preferred embodiment of the novel phospholipid c is 7 and d is 9.

In a preferred embodiment of the process c is 13 and d is 15.

In a preferred embodiment of the process c is 17 and d is 19.

In a preferred embodiment of the process c is 3 and d is 5.

In a preferred embodiment of the process c is 4 and d is 6.

In a preferred embodiment of the process c is 5 and d is 7.

In a preferred embodiment of the process c is 7 and d is 9.

DETAILED DESCRIPTION OF THE INVENTION

The present invention is directed to novel phospholipid compounds, which conform to the following structure:

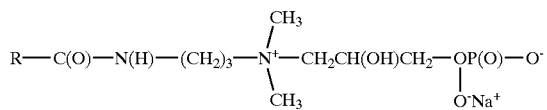

wherein;
R is

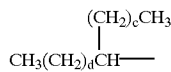

c and d are each integers ranging from 3 to 19 with the proviso that d=c+2.

The compounds of the present invention are prepared by reacting first reacting a guerbet acid with dimethylaminopropyl amine (DMAPA) to give a tertiary amine intermediate.

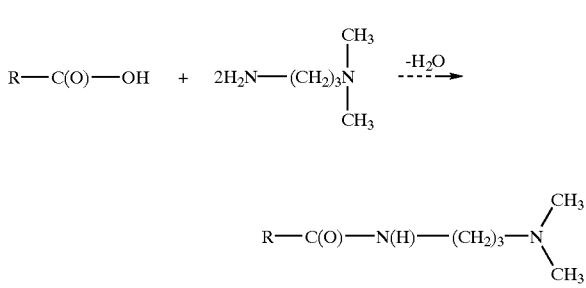

Guerbet Amidoamine

This intermediate is then reacted with 3-chloro-2hydroxypropyl-phosphate made in accordance with the procedure outlined in U.S. Pat. No. 4,283,542 to O'Lenick, incorporated herein by reference.

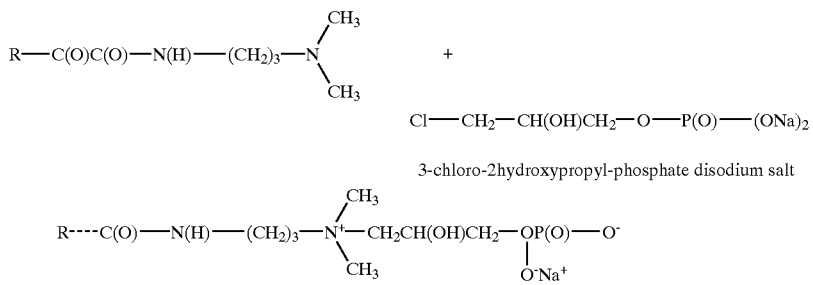

3-chloro-2hydroxypropyl-phosphate disodium salt wherein;
R is:

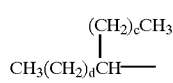

c and d are each integers ranging from 3 to 19 with the proviso that d=c+2.

The compounds of the present invention are made reaction of the intermediate above with the guerbet amido-amine under aqueous conditions. The product of the invention is thereby attained.

The compatibility of these novel phospholipid compounds of the invention with human tissue, i.e., dermal and eye tissue has also been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

EXAMPLES

Dimethyl aminopropyl amine and diethyl aminopropyl amine are items of commerce available from a variety of sources including Dow Chemical.

Epichlorohydrin is an item of commerce available from a variety of sources including Dow Chemical.

Disodium phosphate is an item of commerce available from a variety of sources.

Preparation of Amido Amines

Vista Chemical practices the oxidation of guerbet alcohols commercially. The values of c and d were actually determined by analysis and are not dependant upon trade name for meaning.

| Example | Commercial Name | c | d |
|---|---|---|---|
| 1 | Isocarb 12 | 3 | 5 |
| 2 | Isocarb 14 | 4 | 6 |
| 3 | Isocarb 16 | 5 | 7 |
| 4 | Isocarb 20 | 7 | 9 |
| 5 | Isocarb 32 | 13 | 15 |
| 6 | Isocarb 40 | 17 | 19 |

Isocarb is a trademark of Vista.

Aminopropyl Amine

The compounds conform to the following structure:

Example 7

Dimethyl Aminopropyl Amine

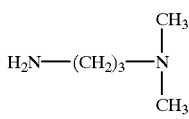

Example 8

Diethyl Aminopropyl Amine

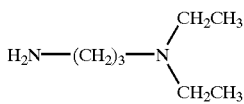

General Procedure

To the specified number of rams the specified amines (Examples 7 and 8 ) is added the specified number of grams of the specified guerbet acid (examples 1–6) under agitation. The temperature of the mass is raised to 180–200° C. and water is stripped off as formed. This temperature is held for between 1 and 12 hours. The acid value and the primary amine value drops to vanishingly small levels and the tertiary amine level approaches theoretical.

The products are clear liquids and are liquid to extraordinary temperatures.

| | Guerbet Acid | | Aminopropyl Amine | |
|---|---|---|---|---|
| Example | Example | Grams | Example | Grams |
| 9 | 1 | 199.0 | 7 | 122.0 |
| 10 | 2 | 227.0 | 7 | 122.0 |
| 11 | 3 | 225.0 | 7 | 122.0 |
| 12 | 4 | 283.0 | 7 | 122.0 |
| 13 | 5 | 311.0 | 7 | 122.0 |
| 14 | 6 | 592.0 | 7 | 122.0 |
| 15 | 1 | 199.0 | 8 | 150.0 |
| 16 | 2 | 227.0 | 8 | 150.0 |
| 17 | 3 | 225.0 | 8 | 150.0 |
| 18 | 4 | 283.0 | 8 | 150.0 |
| 19 | 5 | 311.0 | 8 | 150.0 |
| 20 | 6 | 592.0 | 8 | 150.0 |

Example 21

Preparation of 3-Chloro-2-hydroxypropyl Phosphate Intermediate

To a suitable reaction vessel equipped with reflux condenser, thermometer and agitation is added 142.0 grams of $Na_2PO_4$ and 424.5 grams of de-ionize water. Mix well until a solution is obtained. Next add 141.0 grams of Epichlorohydrin under agitation. Apply heat to 90° C., refluxing back into the vessel any distillate. As the temperature increases to 95–100° C. the contents will clear. Hold at this temperature for 3–4 hours. The resulting product is a 40% aqueous solution of;

$$Cl—CH_2—CH(OH)CH_2—O—P(O)—(O\ Na)_2$$

Preparation of the Phospholipid of the Present Invention

Into a suitable reaction flask is charged the specified amount of of de-ionized water. An aqueous solution of 652.0 grams of 3-chloro-2-hydroxypropyl phosphates Intermediate (Example 21) is next added into the reaction vessel. Heat is applied to 90° C. Next, add the specified number of grams of the specified amidoamine (examples 1–26) is charged into the reaction vessel under good agitation. The temperature is maintained at between 90° C. and 95° C., until the percentage of free tertiary amine is 0.5% maximum. During the reaction time the pH is kept at between 7 and 8 with NaOH as required. The reaction mass will clear when the product is at 90° C. for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

| Example | Example | Grams | Water (Grams) |
|---|---|---|---|
| 22 | 9 | 303.0 | 1560.0 |
| 23 | 10 | 331.0 | 1645.0 |
| 24 | 11 | 329.0 | 1561.0 |
| 25 | 12 | 387.0 | 1813.0 |
| 26 | 13 | 415.0 | 1897.0 |
| 27 | 14 | 696.0 | 2740.0 |
| 28 | 15 | 331.0 | 1645.0 |
| 29 | 16 | 359.0 | 1729.0 |
| 30 | 17 | 357.0 | 1741.0 |
| 31 | 18 | 414.0 | 1890.0 |
| 32 | 19 | 443.0 | 1894.0 |
| 33 | 20 | 743.0 | 2887.0 |

Applications

The compounds of the present invention are liquids, free of rancidity and when applied to the skin from aqueous solution provide good lubrication, a desirable non greasy feel and outstanding emmoliency.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A phospholipid compound of the following structure:

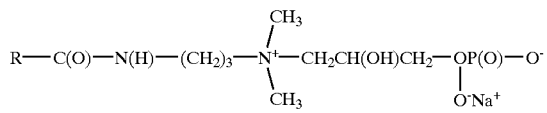

wherein;

R is

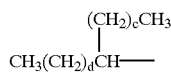

c and d are each integers ranging from 3 to 19 with the proviso that d=c+2.

2. A phospholipid compound of claim 1 wherein c is 13 and d is 15.

3. A phospholipid compound of claim 1 wherein c is 17 and d is 19.

4. A phospholipid compound of claim 1 wherein c is 3 and d is 5.

5. A phospholipid compound of claim 1 wherein c is 4 and d is 6.

6. A phospholipid compound of claim 1 wherein c is 5 and d is 7.

7. A phospholipid compound of claim 1 wherein c is 7 and d is 9.

8. A process for conditioning skin that comprises contacting the skin with an effective conditioning amount of a phospholipid compound of the following structure:

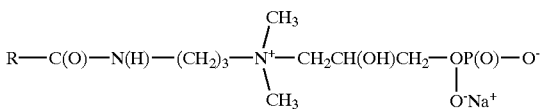

wherein;

R is

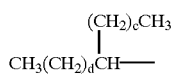

c and d are each integers ranging from 3 to 19 with the proviso that d=c+2.

9. A process of claim 8 wherein the effective conditioning concentration ranges from 0.1% to 15% by weight of the phospholipid.

10. A process of claim 8 wherein c is 13 and d is 15.
11. A process of claim 8 wherein c is 17 and d is 19.
12. A process of claim 8 wherein c is 3 and d is 5.
13. A process of claim 8 wherein c is 4 and d is 6.
14. A process of claim 8 wherein c is 5 and d is 7.
15. A process of claim 8 wherein c is 7 and d is 9.
16. A process of claim 9 wherein c is 13 and d is 15.
17. A process of claim 9 wherein c is 17 and d is 19.
18. A process of claim 9 wherein c is 3 and d is 5.
19. A process of claim 9 wherein c is 4 and d is 6.
20. A process of claim 9 wherein c is 5 and d is 7.

* * * * *